(12) United States Patent
Frazee (10) Patent No.: US 7,243,580 B2
(45) Date of Patent: Jul. 17, 2007

(54) TORQUE LIMITING DRIVER WITH EASILY DISASSEMBLED COMPONENTS FOR STERILIZATION

(75) Inventor: Edmund W. Frazee, Cromwell, IN (US)

(73) Assignee: DePuy Products, Inc., Warsaw, IN (US)

( * ) Notice: Subject to any disclaimer, the term of this patent is extended or adjusted under 35 U.S.C. 154(b) by 538 days.

(21) Appl. No.: 10/746,107

(22) Filed: Dec. 23, 2003

(65) Prior Publication Data

US 2005/0148905 A1    Jul. 7, 2005

(51) Int. Cl.
*B25B 23/14*    (2006.01)
(52) U.S. Cl. ............................. 81/467; 81/439; 81/471
(58) Field of Classification Search ............... 81/58, 81/467, 438, 439, 58.4, 441, 471, 476–480; 73/862.23; 606/101, 104
See application file for complete search history.

(56) References Cited

U.S. PATENT DOCUMENTS

| | | | | |
|---|---|---|---|---|
| 4,838,264 A | * | 6/1989 | Bremer et al. | 606/104 |
| 5,295,831 A | * | 3/1994 | Patterson et al. | 433/141 |
| 5,725,533 A | * | 3/1998 | Carlsson | 606/101 |
| 6,308,598 B1 | * | 10/2001 | O'Neil | 81/467 |
| 6,439,086 B1 | * | 8/2002 | Bahr | 81/467 |
| 7,127,955 B2 | * | 10/2006 | Bondhus et al. | 73/862.23 |

* cited by examiner

*Primary Examiner*—Lee D. Wilson
*Assistant Examiner*—Anthony Ojini
(74) *Attorney, Agent, or Firm*—Maginot, Moore & Beck (57) ABSTRACT

A driver has components that are easily disassembled for cleaning and/or sterilization. Once disassembled, the limited number of components allows for easy reassembly. The driver utilizes a cam that rides on spring fingers for determining the level of producible torque that the driver can produce. The cam and spring fingers are contained in a housing. Particularly, the spring fingers are part of a finger housing that is key lockable with the housing when assembled for movement as one unit. The cam is integral with a driver shaft and is received within the finger housing. The cam and driver shaft are limitedly rotatable with respect to the finger housing. The level of producible torque may be changed by providing cams and/or spring fingers of various dimensions. The driver is torque-limiting in one direction (tightening) and essentially non torque-limiting in the opposite direction (loosening). The various components are also large enough to be easily handled reducing the chance of lost components.

37 Claims, 7 Drawing Sheets

TORQUE LIMITING DRIVER WITH EASILY DISASSEMBLED COMPONENTS FOR STERILIZATION

BACKGROUND

1. Field of the Invention

The present invention relates to devices for applying a particular level of torque to an orthopedic implant component and, more particularly, to a torque limiting driver for applying a particular level of torque to an orthopedic implant component that can be easily disassembled for sterilization of the torque limiting driver components.

2. Background Information

Various types of orthopedic implants such as spine implants and joint prosthetics typically utilize and/or rely on components that must be securely attached to other components of the implant or to various parts of the body. The integrity and/or effectiveness of the implant may depend upon proper attachment of the component. Particularly, if the component is either over-tightened or under-tightened, there can be associated negative effects. For example, an under-tightened component may loosen causing the loss of effectiveness of a component, while an over-tightened component may impart an undesirable amount of stress on one or more components.

Implants are thus attached using devices that will allow the surgeon to apply the necessary torque throughout the attachment process, since a certain level of torque is required to properly secure a component. It is often difficult, however, to ascertain when the proper level of torque has been imparted on an implant component and, in turn, when the implant component has been securely attached.

In order to alleviate these problems, torque-limiting devices or drivers have been developed to help ensure that a consistent or limited assembly torque is imparted on implant components in order to properly secure torque-applied implant components to other implant components and/or body parts. Torque-limiting drivers are calibrated to impart a desired level of torque to an implant component during implant thereof. Other torque-limiting drivers offer user adjustable calibration for varying the level of applied torque. A problem with these prior art torque-limiting drivers is their complexity and/or their ability to be disassembled for cleaning. Another problem with these prior art torque-limiting drivers is there lack of being able to be medically sterilized.

Current federal regulations (e.g. FDA regulations) do not require medical instruments to be able to be disassembled. It is anticipated, however, that future federal regulations will require that some or all medical instruments be able to be disassembled, especially for complete sterilization of the instrument.

Because, as pointed out above, current torque-limiting drivers cannot be disassembled or they include parts that can be medically sterilized, there exists a need for a torque-limiting driver that can be disassembled for medical sterilization. There is also a need for a torque-limiting driver that can be easily reassembled after medical sterilization.

SUMMARY

The subject invention is a driver that may be easily disassembled for cleaning and/or sterilization of its various components and then easily reassembled. The driver provides a fixed level of torque in one direction of rotation thereof. The fixed level of torque may be changed by altering the configuration of a component thereof.

Once disassembled, the limited number of components allows for easy reassembly. The driver utilizes a cam that rides on one or more torque, cam or spring fingers for determining the level of producible torque that the driver can produce. The cam and torque finger(s) are disposed in a handle. The torque fingers may be part of a finger housing that is key lockable with the handle for movement as one unit, with the cam separate from the finger housing and removable therefrom. The handle may alternatively integrally include the torque finger(s), with the cam being separate from the handle and removable therefrom. The cam may be integral with a driver shaft and is received within the finger housing and/or handle. The cam and driver shaft are limitedly rotatable with respect to the finger(s).

The level of producible torque may be changed by providing cams of various configurations, and/or fingers of various elasticity or spring force. The driver is torque-limiting in one direction of rotation (i.e. an implant component tightening direction) and essentially non-torque-limiting in the opposite direction of rotation (i.e. an implant component loosening direction). The various driver components are also large enough to be easily handled thereby reducing the chance of lost driver components during disassembly thereof.

In one form, there is provided a driver having a handle having an interior supporting a first cam finger, a shaft component having a component driver shaft on one end thereof and removably received in the handle interior whereby at least a portion of the component driver shaft is exterior of the handle, a cam disposed on the shaft component so as to be within the handle interior when the shaft component is received in the handle interior and configured to cooperate with the cam finger to provide up to a given level of torque to the component driver shaft when the handle is rotated in a first direction and to provide up to an equal or greater (up to the mechanical strength properties thereof) level of torque to the component driver shaft when the handle is rotated in a second direction, and a cap removably receivable on the handle and operative to retain the cam and the shaft component within the handle interior.

In another form there is provided a driver having a handle having a keyed handle interior, a sleeve having a sleeve interior and an outer configuration configured to be removably received in the keyed handle interior and to rotatably move with the handle, a cam finger associated with the sleeve a shaft component having a drive shaft portion at one end thereof and configured to be removably received in the sleeve interior, a cam disposed on the shaft component and configured to cooperate with the cam finger to provide up to a given level of torque to the drive shaft portion in a first direction of rotation of the handle and to provide up to an equal or greater (up to the mechanical strength properties thereof) level of torque to the drive shaft portion in another direction of rotation of the handle, and a cap removably received on an end of the handle, the cap having a bore allowing the drive shaft portion of the shaft component to extend therethrough and adapted to releasably retain the sleeve, the cam and the shaft component in the handle interior.

In yet another form, there is provided a driver that includes a handle assembly having an interior and a first cam finger. The driver further includes a shaft assembly partially received in the interior of the handle assembly, the shaft assembly having a component driver shaft located outside of the interior of the handle assembly. Also, the driver includes a cam disposed on the shaft component and positioned in the interior of the handle assembly and configured to cooperate with the cam finger to provide up to a first level of torque to the component driver shaft when the handle assembly is rotated in a first direction. Further, the driver includes a cap removably receivable on the handle assembly and configured to retain the shaft assembly at least partially received within the interior of the handle assembly.

In still another form, there is provided a driver that includes a handle having a keyed handle interior. The driver further includes a sleeve having a sleeve interior and an outer configuration configured to be removably received in the keyed handle interior and to rotatably move with the handle. The driver further includes a cam finger associated with the sleeve. Additionally, the driver includes a shaft component having a drive shaft portion at one end thereof and configured to be removably received in the sleeve interior. Moreover, the driver includes a cam disposed on the shaft component and configured to cooperate with the cam finger to provide up to a given level of torque to the drive shaft portion in a first direction of rotation of the handle and to provide up to an equal or greater level of torque to the drive shaft portion in another direction of rotation of the handle. In addition, the driver includes a cap removably received on an end of the handle, the cap having a bore allowing the drive shaft portion of the shaft component to extend therethrough and adapted to releasably retain the sleeve, the cam and the shaft component in the handle interior.

BRIEF DESCRIPTION OF THE DRAWINGS

In the drawings.

Corresponding reference characters indicate corresponding parts throughout the several views. Like reference characters tend to indicate like parts throughout the several views.

DESCRIPTION OF THE PREFERRED EMBODIMENT(S)

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention.

Figure 1:
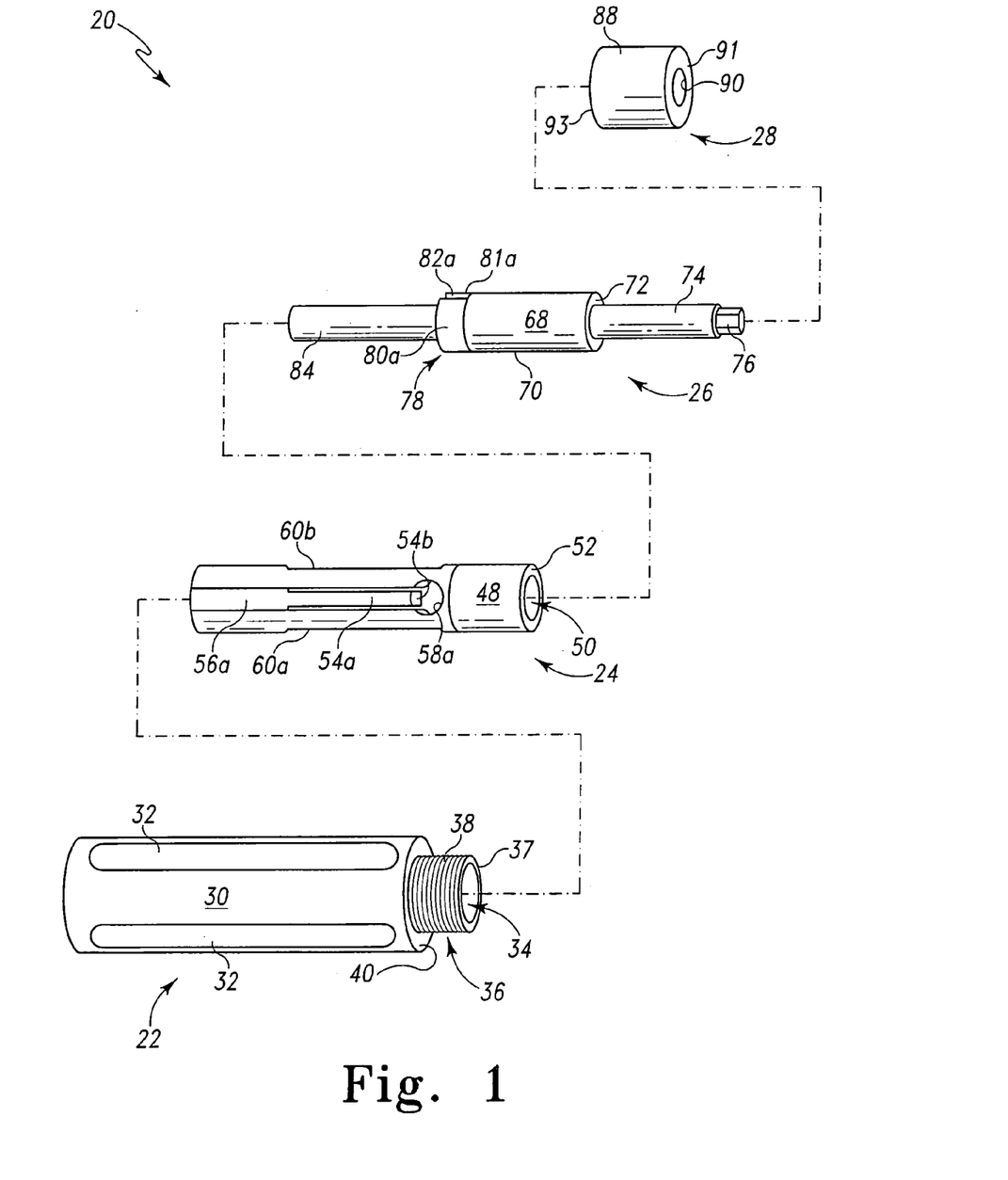
FIG. 1 is an exploded perspective view of the present driver in accordance with the principles of the present invention.

Referring now to FIG. 1 there is shown an exploded perspective view of an exemplary torque-limiting driver, generally designated 20, in accordance with the principles of the subject invention. In the exemplary form, the driver 20 includes a handle or handle component 22, a sleeve or sleeve component 24, a shaft or shaft component 26 and an end cap 28. As represented by the arrows, the handle component 22 receives the sleeve component 24, the sleeve component 24 receives the shaft component 26, and the end cap 28 is received over a portion of the shaft component 26 and received onto a portion of the handle component 22.

The driver 20 is adapted, configured and/or operative to provide a fixed level of torque when the handle 22 of the driver 20 is rotated in one or a first direction (i.e. an implant component tightening direction) and an equal or greater (up to the mechanical strength properties thereof) or essentially non-torque-limiting level of torque (dependent upon rotational force applied to the handle 22) in another or second direction (i.e. an implant component loosening direction). It should be appreciated that the nomenclature first and second are arbitrary. Moreover, the direction or rotation for loosening and tightening may be either right or left handed. Typically, and preferably, the driver 20 is right handed such that clockwise rotation is tightening and counterclockwise rotation is loosening. It should further be appreciated that while the present driver 20 provides a fixed level of torque, the particular level of torque may be selected and thus changed by changing out one or more of the components of the driver. In other words, with a particular component or set of components, the driver 20 provides a particular level of torque. With another configuration of component or components, other fixed levels of torque may be provided. The driver 20 may therefore come with a set of components that each provides a particular level of torque.

Figure 2:
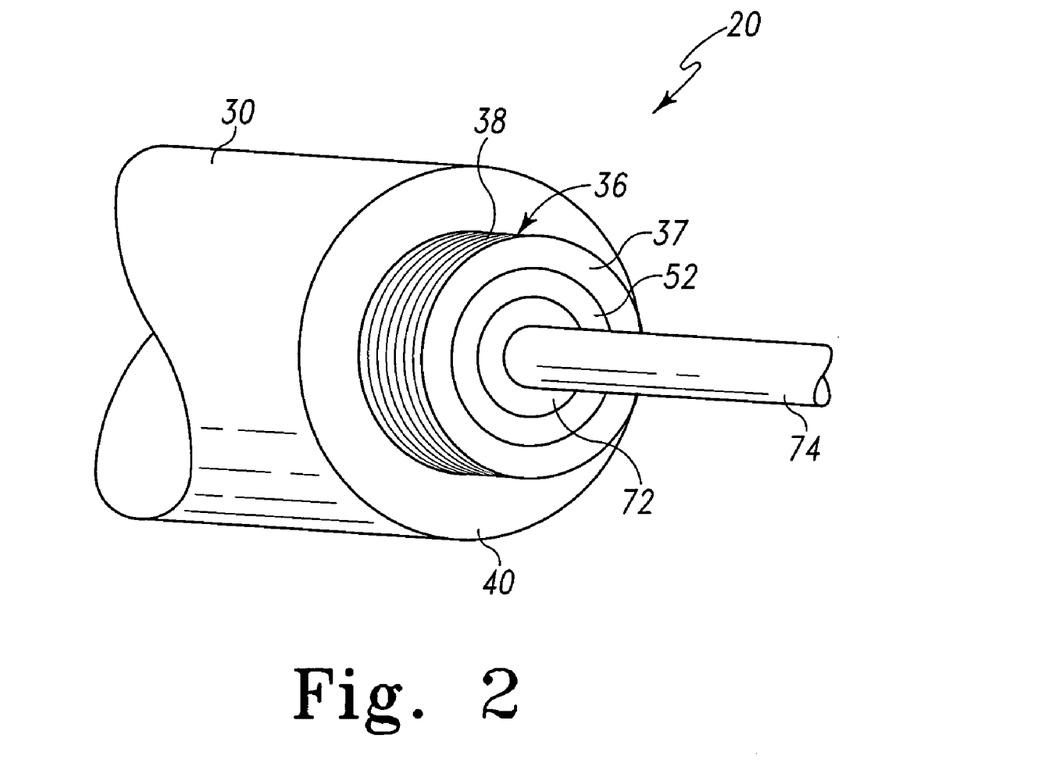
FIG. 2 is an enlarged partial perspective view of the assembled driver of FIG. 1 particularly illustrating the manner of final assembly.

Referring additionally to FIG. 2, an end of the driver 20 is shown. The components 22, 24, and 26 (i.e. the handle 22, the sleeve 24 and the shaft 26) have been assembled together, while the end cap 28 has not been yet attached to the handle 22. FIG. 2 illustrates that when assembled, the end 52 of the body 48 of the sleeve 24 is flush with the end 37 of the neck 36 of the body 30 of the handle 22. Additionally, the end 72 of the intermediate section 70 of the body 70 of the shaft 26 is flush with the end 37 of the neck 36 of the body 30 of the handle 22. The driver shaft portion 74 of the shaft component 36 axially extends from the ends thereof. When the end cap 28 is received on the neck 36 of the body 30 of the handle 22, the driver shaft portion 74 extends through the bore 90 of the end cap 28. The end cap 28 is threadedly received on the neck 36 of the body 30 of the handle 22. The driver shaft portion 74 of the body 68 of the shaft component 26 is thus free to rotate as appropriate through the bore 90.

Figure 3:
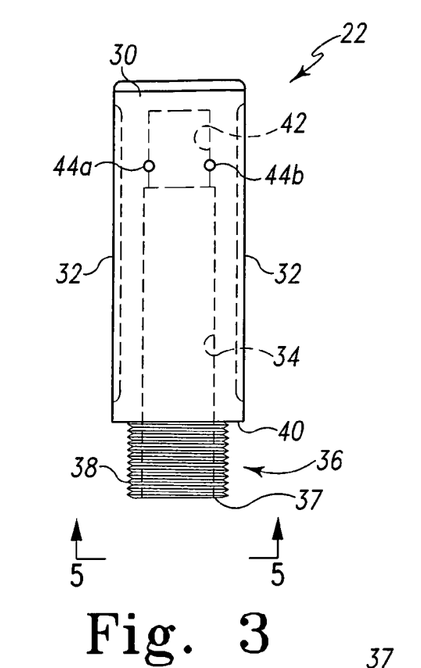
FIG. 3 is a side plan view of the handle of the driver of FIG. 1 in accordance with the principles of the subject invention.
Figure 4:
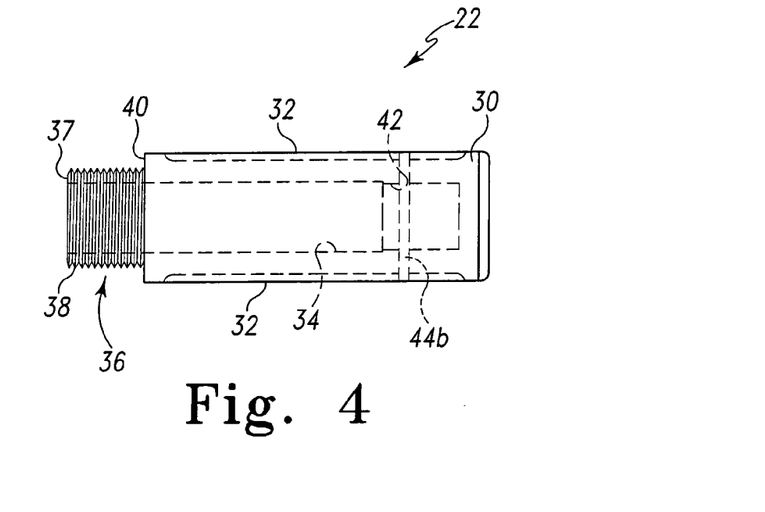
FIG. 4 is a side plan view of the handle of the driver rotated 90° from the view of FIG. 3.
Figure 5:
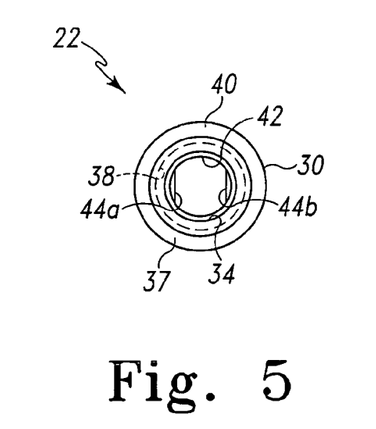
FIG. 5 is a plan view of an end of the handle of FIG. 3 taken along line 5—5 thereof.

Referring additionally to FIGS. 3–5, the handle component (handle) 22 is particularly shown. As indicated above, the handle 22 is defined by a body 30 that in a preferred form is fabricated from a plastic or polymer that is appropriate for surgical use and which can be repeatedly sterilized. The body 30 is shown as a cylinder of a particular diameter. The diameter of the body 30 is sized to be comfortably grasped by the user. The body 30 includes a number of troughs or channels 32 formed longitudinally in the outer surface thereof. The troughs 32 allow the user (e.g. surgeon) to adequately grip the handle during use. The handle 22 also has a neck 36 axially extending from the body 30. The neck 36 has a diameter that is less than the diameter of the body 30. The neck 36 includes threading 38 on an outside surface thereof. The threading 38 is adapted to receive complementary threading of the end cap 28.

The body 30 also includes a bore 34 that extends from the end 37 of the neck 36. The bore 34 includes a reduced diameter portion 42 distal from the end 37. Additionally, the bore 34 is keyed. Particularly, the bore 34 is keyed in order for the sleeve 24 to rotate along with the handle 22. The keyed bore 34 is provided through pins 44a and 44b disposed on opposite sides (180° from each other) of the bore 34. As best seen in FIG. 5, this creates a round key with a flat on either side. The sleeve 24 thus is only fully received into the bore 34 when the sleeve is axially inserted therein in the proper rotational orientation. In this manner, as the handle 22 is rotated, the sleeve 24 must rotate therewith.

Figure 6:
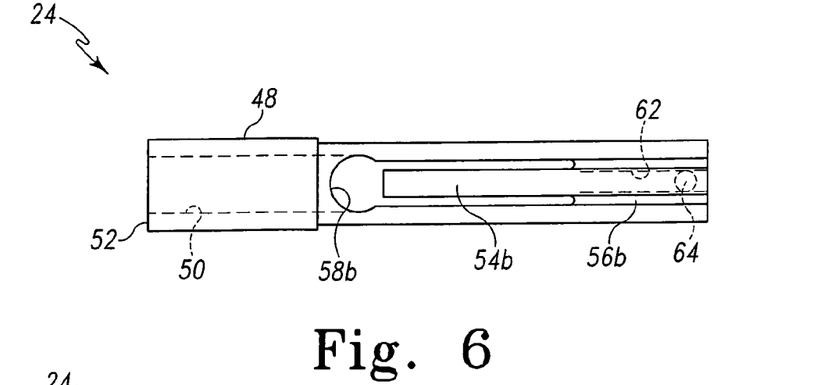
FIG. 6 is a side plan view of the cam spring finger sleeve of the driver of FIG., 1 in accordance with the principles of the subject invention.
Figure 7:
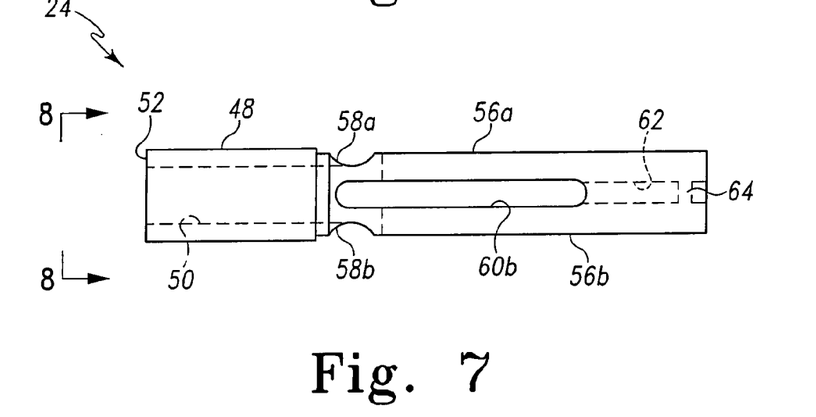
FIG. 7 is a side plan view of the cam spring finger sleeve rotated 90° from the view of FIG. 6.
Figure 8:
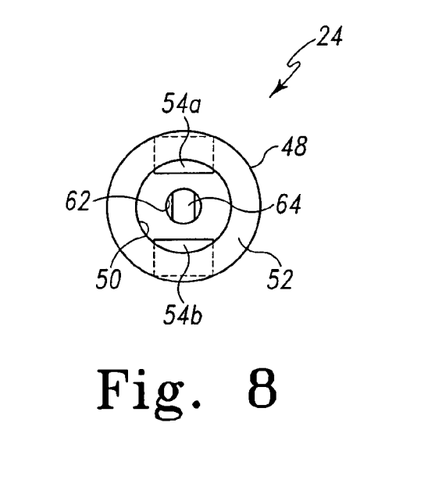
FIG. 8 is a plan view of an end of the cam spring finger sleeve of FIG. 6 taken along line 8—8 thereof.

Referring additionally to FIGS. 6–8, the sleeve component (sleeve) 24 is particularly shown. The sleeve 24 is defined by a body 48 that is preferably fabricated from a metal that is suitable for surgical use, withstands applied bending in an amount necessary for functioning in the manner described herein, and which may be repeatedly sterilized. The body 48 is tubular or cylindrical in shape and has an outer diameter that will be received in the bore 34 of the handle 22. It is preferable that the outer diameter of the sleeve 24 is only slightly less than the inner diameter of the bore 34 in order to prevent wobble of the sleeve 24 within the bore 34.

The body 48 has a bore 50 that extends axially through the length of the body. The bore 50 is of a diameter that will accommodate the intermediate portion 70 of the body 68 of the cam/driver shaft 26. The bore 50 has a reduced diameter bore portion 62 at an end distal to the end 52. The reduced diameter bore portion 62 is sized to rotatably accommodate the diameter of the stabilization shaft portion 84 of the body 68 of the shaft component 26. A stop in the form of a pin 64 is disposed in the bore portion 62. The stop 64 prevents travel of the shaft 84 outside of the sleeve 24.

A pair of elongated windows 60a (see FIG. 1) and 60b are formed in the body 48. The windows are diametrically opposite one another (i.e. disposed 180° from one another) in the body 48. The windows 60a, 60b allow the free rotation of the cam 78 of the body 68 of the cam/driver shaft component 26 and provide for proper fabrication of the sleeve 24. A pair of diametrically opposite (i.e. 180°) openings 58a and 58b are formed in the body 48. Each opening 58a, 58b is disposed 90° from the windows 60a and 60b. The openings allow for proper fabrication of cam fingers, cam followers or the like 54a and 54b.

Each cam finger is configured to provide a given tension or force against a cam surface of the cam. Each cam finger provides a spring or spring-like mechanism that provides pressure against the cam surface, particularly during (attempted) rotation. This translates to resistance against rotation of the handle as each finger rides along a cam surface. The greater the height of the cam surface, the greater the torque required for each cam finger to ride to and over the cam peak associated with the cam surface. The spring force of each finger may be changed to alter the applied torque level. This may be done in conjunction with various cam configurations.

Cam fingers 54a and 54b are disposed 90° from the windows 60a and 60b and diametrically opposite (i.e. 180°) from each other. Each finger is disposed in a side of the body 48 each having a respective flat 56a and 56b. The flats create a keying of the body 48 that corresponds to the keying of the bore 34 of the body 30 of the handle 22. As best seen in FIG. 8, each spring finger 54a, 54b extends slightly into the bore 50. This provides the interaction between the fingers and the cam 78 as described in detail below. Briefly, the fingers interact or cooperate with the cam to provide the fixed level of torque in the first direction of rotation and the unlimited level of torque in the second direction of rotation. It should be appreciated that the sleeve may be fabricated with a single spring finger or more than two spring fingers as shown. Additionally, the form of the fingers may be changed as appropriate but operatively in accordance with the principles of the subject invention.

It should be appreciated that the features of the sleeve 24, including the cam fingers 54, may be fashioned as a handle. In this case, the sleeve 24 may incorporate features of the handle 22. This eliminates a component and makes the driver a three-component device. Other variations are contemplated.

Figure 9:
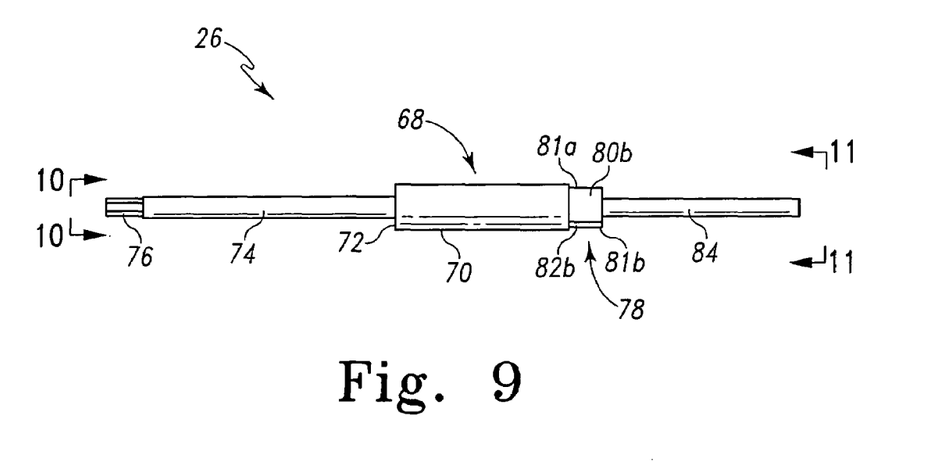
FIG. 9 is a side plan view of the cam/driver shaft of the driver of FIG. 1 in accordance with the principles of the subject invention.
Figure 10:
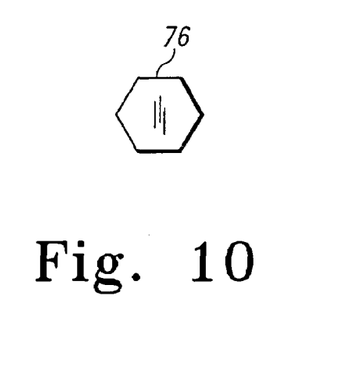
FIG. 10 is an end view of the cam/driver shaft of FIG. 9 taken along line 10—10 thereof.
Figure 11:
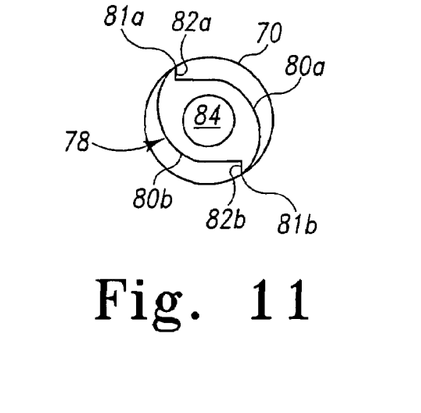
FIG. 11 is an end view of the cam/driver shaft of FIG. 9 taken along line 11—11 thereof.

Referring additionally to FIGS. 9–11, there is depicted the shaft component 26 that may be termed a cam/driver shaft 26. The cam/driver shaft 26 is defined by a body 68 that is preferably fabricated from a metal that is suitable for surgical use, withstands applied torque in an amount necessary for functioning in the manner described herein, and which may be repeatedly sterilized. The body 68 includes an intermediate or cam support section or portion 70 that is generally cylindrical in shape. The diameter of the cam support section 70 is sized to be received in the bore 50 of the sleeve 24. The cam support section 70 has a cam 78 on one end thereof. A stop shaft 84 extends from the end of the cam 78. A driver shaft 74 extends from an end of the cam support section 70 opposite the cam 78. The driver shaft 74 terminates in a driver end or driver 76. As best seen in FIG. 10, the driver 76 is configured as a hexagon for receipt in a hexagon bore of an implant component (not shown). Other shapes may be utilized such as a star-shape (e.g. used on a Torx® device). The driver shaft 74 is sized to extend out from the end cap 28 when the cam/driver shaft 26 is installed in the handle 22.

The cam 78, as best seen in FIG. 11, is shaped to provide a fixed level of torque to the driver shaft 74 with the cooperation and/or co-action of the spring fingers 54a and 54b with the cam 78. Upon reaching the particular level of torque, the cam allows the driver shaft 74 to slip to a minimum level of torque. The cam 78 has two, variably sloped cam surfaces 80a and 80b that are disposed about the stabilizer shaft 84. The cam surfaces 80a and 80b end in respective peaks 81a and 81b. Two, diametrically opposed cam stops 82a and 82b are respectively defined between the cam peaks 81a and 82b and the cam surfaces 80a and 80b. The cam/driver shaft 26 is operative to stay fixed against rotation while the handle 22 and thus the sleeve 24 rotate thereabout when the driver 76 is received in an implant component and the handle 22 is rotated.

It should be appreciated that the cam/driver shaft 26 may come in various configurations. Particularly, the driver end 76 may have a shape other than a hexagon in order to accommodate implant components such as screws that have socket configurations other than hexagon. Additionally, a set of cam/driver shafts may be provided that come in a variety of cam configurations and/or driver ends for providing a variety of torque levels and for accommodating various types of implant components.

Alternatively, the cam 78 may be formed with a single cam finger surface and one peak rather than with two surfaces/peaks as shown. This allows for a more incremental applied torque. The amount of handle rotation required to go from a minimum applied torque (tightening) to the maximum level of applied torque (tightening) would, however, increase. The number of cam fingers typically corresponds to the number of cam surfaces. The more cam fingers/surfaces, the less amount of handle rotation necessary to reach the maximum driver torque from the least driver torque. Actual amount of maximum driver torque would still depend on the cam surface configuration and/or stiffness of the cam finger(s). The sleeve and/or handle would incorporate the requisite number of cam fingers and/or be configured to accommodate the particular cam configuration (the cam/driver shaft component).

Figure 12:
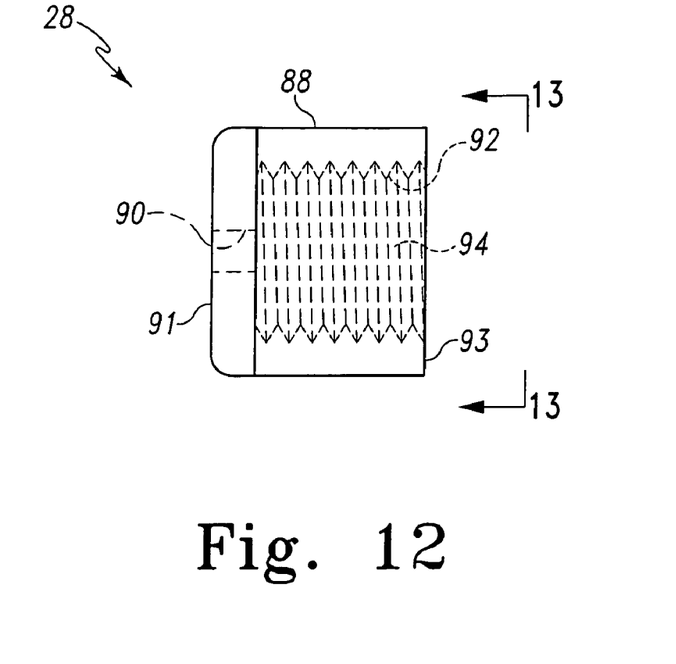
FIG. 12 is a side view of the end cap of the driver of FIG. 1 in accordance with the principles of the subject invention.
Figure 13:
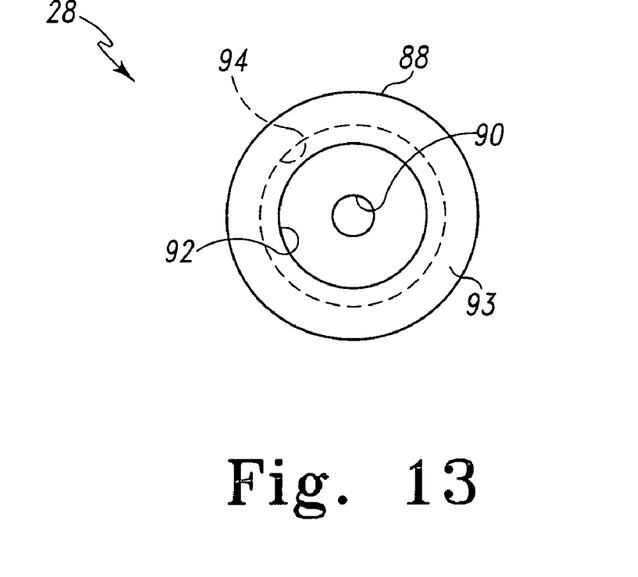
FIG. 13 is an end view of the end cap of FIG. 12 taken along line 13—13 thereof.

With reference to FIGS. 12 and 13, the end cap 28 is depicted. The end cap 28 is defined by a body 88 that in a preferred form is fabricated from a plastic or polymer that is appropriate for surgical use and which can be repeatedly sterilized. The body 88 is cylindrical in shape and has a large diameter bore 92 in an end 93 thereof that has internal threads 94. The bore 92 and associated threads 94 are sized to be received over and by the neck 36 and thread 38 of the handle 22. The shaft 90 is disposed in the end 91 of the body 88 of the end cap 28. The bore 90 provides communication between the interior 92 of the end cap body 88 and outside of the driver 20. When the end cap 28 is received on neck 26 of the handle 22, the end 93 abuts the end 37 of the neck 36.

Figure 14:
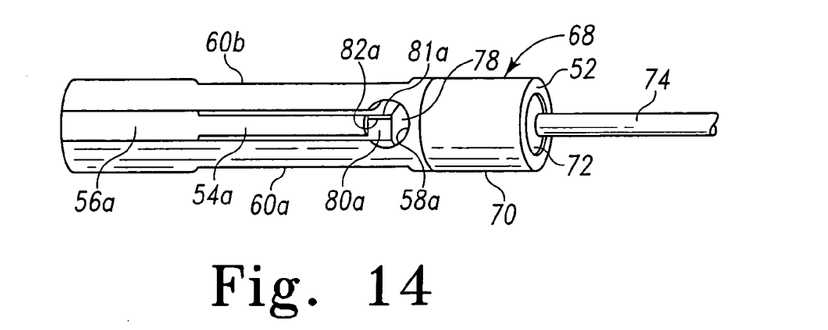
FIG. 14 is a partial, enlarged perspective view of the cam/driver shaft assembled into the cam spring finger sleeve.

In FIG. 14, there is depicted the cam/driver shaft 26 disposed in the sleeve 24 for clarity in the understanding of the principles of the subject invention. Particularly, the cam 78 is shown in the sleeve 24 in relation to the spring finger 54a. The spring finger 54b is not visible in the view of FIG. 14, nor is the other side of the cam 78. The cam/driver shaft is situated in the sleeve 24 such that the cam 78 is viewable in the opening 58a. When properly positioned, the cam surfaces 80a and 80b ride underneath and are contacted by spring fingers 54a and 54b. Rotation of the sleeve 24 is accomplished by rotation of the handle 22 since the sleeve 24 is keyed to the handle 22.

The dynamics of the interaction between the spring fingers 54a, 54b and the cam 78 (i.e. the various cam features of the cam surfaces 80a, 80b, the cam peaks 81a, 81b, and the cam stops 82a, 82b) will now be described with reference to FIGS. 15A–C.

Figure 15A:
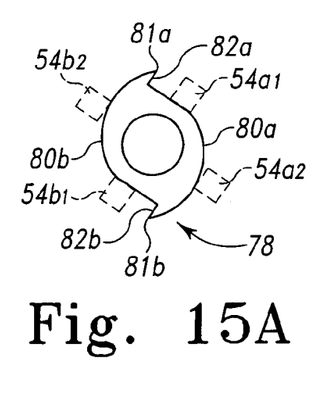
FIG. 15A is an illustration for understanding operation of the driver of FIG. 1 in accordance with the principles of the subject invention, particularly action between the cam of the cam/driver shaft and the spring fingers of the cam spring finger sleeve.
Figure 15B:
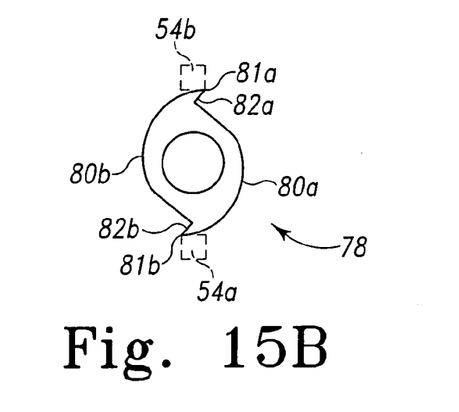
FIG. 15B is an illustration for understanding operation of the driver of FIG. 1 in accordance with the principles of the subject invention, particularly action between the cam of the cam/driver shaft and the spring fingers of the cam spring finger sleeve.
Figure 15C:
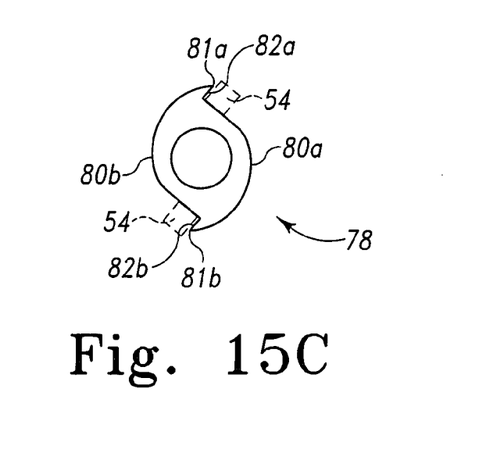
FIG. 15C is an illustration for understanding operation of the driver of FIG. 1 in accordance with the principles of the subject invention, particularly action between the cam of the cam/driver shaft and the spring fingers of the cam spring finger sleeve showing.

Referring to FIG. 15A, two sets of spring fingers 54a1, 54b1 and 54a2, 54b2 are shown for showing the positions the spring fingers may take. While as pointed out herein that the sleeve 24 may have more than two spring fingers, FIG. 15A is not a representation of that case. When the spring fingers are in the position as shown in 54a1, 54b1 and they are turned in a clockwise direction relative to FIG. 15A, gradually continuing torque is produced as the fingers ride up the slope of the respective cam surface 80a, 80b. As the fingers reach the position of 54a2, 54b2, it becomes harder to twist or rotate the handle 22. This is due to the tendency of the spring fingers to resist radially outward movement as the force against the spring fingers is produced by the sloped cam surfaces. Maximum torque is achieved when the fingers are in the position of FIG. 15B (where the fingers are labeled 54a and 54b.) or at the peaks 81a, 81b of the cam 78. The fingers 54a, 54b are radially outward biased against a natural inward biasing force of the fingers. Continued rotation force on the handle 22 causes the fingers 54 to fall off the peaks 81a, 81b (slip) thereby reducing the applied torque.

Referring back to FIG. 15A, when fingers 54a2, 54b2 move in the counterclockwise direction illustrated as then moving to the position occupied by fingers 54a1, 54b1, the handle turns without movement of the driver shaft 74. This occurs until the fingers reach the stops 81a, 81b as illustrated in FIG. 15C. At this point, continued counterclockwise movement of the fingers 54 against the stops 81a, 81b provides unlimited torque (as much as can be applied by the user) in order to provide loosening of a component. The spring fingers 54 cannot ride over the stops 81a, 81b.

Thus, in one direction the present driver provides a small amount of torque up to a fixed maximum level of torque (torque-limiting) for driving or tightening a component, and a non torque-limiting amount in another direction for loosening a component.

Also note that while the handle 22 and the end cap 28 were described as being made of plastic, and the sleeve 24 and the shaft 26 were described as being made of metal, it should be appreciated that handle 22 and the end cap 28 may be made of metal, and the sleeve 24 and the shaft 26 may be made of plastic. Alternatively, all these components 22, 24, 26, 28 may be metal, or they may all be made of plastic. Further as an alternative, all these components 22, 24, 26, 28 may be made from any other material(s) that is suitable to undergo a standard medical sterilization process.

There is a plurality of advantages of the subject invention arising from the various features of the subject invention described herein. It will be noted that further alternative embodiments of the subject invention may not include all of the features described yet still benefit from at least some of the advantages of such features. Those of ordinary skill in the art may readily devise their own implementations of the subject invention that incorporate one or more of the features of the subject invention and that fall within the spirit and scope of the subject invention.

What is claimed is:

1. A driver comprising:

a handle assembly having an interior and a first cam finger;

a shaft assembly partially received in said interior of said handle assembly, said shaft assembly having a component driver shaft located outside of said interior of said handle assembly;

a cam disposed on said shaft component and positioned in said interior of said handle assembly and configured to cooperate with said cam finger to provide up to a first level of torque to said component driver shaft when said handle assembly is rotated in a first direction; and a cap removably receivable on said handle assembly and configured to retain said shaft assembly at least partially received within said interior of said handle assembly.

2. The driver of claim 1, wherein said cam is further configured to provide up to a second level of torque to said component driver shaft when said handle assembly is rotated in a second direction.

3. The driver of claim 2, wherein said first level of torque is different from said second level of torque.

4. The driver of claim 3, wherein said first level of torque is less than said second level of torque.

5. The driver of claim 2, wherein said handle assembly includes a second cam finger and said cam provides two cam surfaces each one of which is configured to cooperate with said first and second cam fingers to provide up to the first level of torque to said component driver shaft when said handle assembly is rotated in a first direction and provide up to the second level of torque to said component driver shaft when said handle assembly is rotated in a second direction.

6. The driver of claim 5, wherein said first and second cam fingers and said first and second cam surfaces reduces amount of rotation required to go from a minimum level of torque to a maximum level thereof with respect to a single cam finger and cam surface.

7. The driver of claim 1, wherein:
said handle assembly and said cap are formed of plastic; and
said driver shaft component is formed of metal.

8. The driver of claim 1, wherein said first direction provides tightening of an implant component driven by said component drive shaft, and said second direction provides loosening of an implant component driven by said component drive shaft.

9. The driver of claim 1, wherein said cam is formed integral with said shaft component.

10. The driver of claim 1, wherein configuration of said cam determines the level of torque that can be provided to said component driver shaft in said first direction.

11. A driver comprising:
a handle having a keyed handle interior;
a sleeve having a sleeve interior and an outer configuration configured to be removably received in said keyed handle interior and to rotatably move with said handle;
a cam finger associated with said sleeve;
a shaft component having a drive shaft portion at one end thereof and configured to be removably received in said sleeve interior;
a cam disposed on said shaft component and configured to cooperate with said cam finger to provide up to a given level of torque to said drive shaft portion in a first direction of rotation of said handle and to provide up to an equal or greater level of torque to said drive shaft portion in another direction of rotation of said handle; and
a cap removably received on an end of said handle, said cap having a bore allowing said drive shaft portion of said shaft component to extend therethrough and adapted to releasably retain said sleeve, said cam and said shaft component in said handle interior.

12. The driver of claim 11, wherein said cam is formed integral with said shaft component.

13. The driver of claim 11, wherein said handle and said cap are formed of a polymer, and said sleeve, shaft component and said cam are formed of metal.

14. The driver of claim 11, wherein said configuration of said cam determines said given level of torque.

15. The driver of claim 11, wherein said cam finger determines said given level of torque.

16. The driver of claim 11, wherein said sleeve includes a second cam finger and said cam is configured to cooperate with said first and second cam fingers to provide up to the given level of torque to said drive shaft portion when said handle is rotated in a first direction and provide up to the equal or greater level of torque to said drive shaft portion when said handle is rotated in a second direction.

17. The driver of claim 11, wherein said keyed interior defines a flat and said outer configuration of said sleeve includes a corresponding flat.

18. The driver of claim 11, wherein said keyed interior of said handle is formed by at least one pin inserted transverse to an axis of said interior.

19. A driver comprising:
a handle having a handle interior;
a first member having a first member interior and configured for removable receipt in said handle interior, said first member including first and second cam fingers;
a second member configured for removable receipt in said first member interior, said second member having a drive shaft terminating in a component driver;
a cam carried by said second member, said cam configured to cooperate with said first and second cam fingers to provide up to a first level of torque to said component driver in a first direction of rotation of said; and
a cap removably received on an end of said handle, said cap having a bore allowing a portion of said drive shaft terminating in said component driver to extend therethrough and adapted to releasably retain said first member, said second member, and said cam in said handle interior.

20. The driver of claim 19, wherein said cam is further configured to provide up to a second level of torque to said component driver shaft when said handle is rotated in a second direction.

21. The driver of claim 20, wherein said first level of torque is different from said second level of torque.

22. The driver of claim 21, wherein said first level of torque is less than said second level of torque.

23. The driver of claim 19, wherein said first member comprises a sleeve and said first and second cam fingers are carried by said sleeve.

24. The driver of claim 19, wherein said first and second members are formed of a metal, and said handle and said cap are formed of a polymer.

25. The driver of claim 19, wherein said cam is formed integral with said second member.

26. The driver of claim 19, wherein said configuration of said cam determines said torque-limiting level of torque.

27. The driver of claim 19, wherein said handle interior is keyed and said first member has an outer configuration that is keyed in the same manner as said keyed interior.

28. The driver of claim 27, wherein said keyed handle interior comprises first and second handle interior flats, and said first member keyed outer configuration comprises first and second first member outer configuration flats.

29. The driver of claim 28, wherein said first and second handle interior flats are disposed diametrically opposite one another, and said first and second first member outer configuration flats are disposed diametrically opposite one another.

30. The driver of claim 19, wherein said component driver possesses a hexagonal shape.

31. A driver comprising:
- a sleeve assembly defining a first interior space and having at least one cam finger; and
- a driver assembly having (i) a cam positioned in said first interior space and in contact with said at least one cam finger, and (ii) a driver positioned outside of said interior space;
- wherein said cam is configured to provide a first torque-limiting level of torque to said driver assembly when said handle is rotated in a first direction.

32. The driver of claim 31, wherein said cam is further configured to provide a second torque-limiting level of torque to said driver when said handle is rotated in a second direction.

33. The driver of claim 32, wherein said first torque-limiting level of torque is different from said second torque-limiting level of torque.

34. The driver of claim 33, wherein said first torque-limiting level of torque is less than said second torque-limiting level of torque.

35. The driver of claim 31, further comprising:
- a handle defining a second interior space, wherein (i) said sleeve assembly is positioned within said second interior space, and (ii) said handle has a first threaded portion; and
- a cap having a second threaded portion configured to mate with said first threaded portion, said cap being configured to retain said sleeve assembly within said second interior space of said handle when said first threaded portion is mated with said second threaded portion.

36. The driver of claim 31, wherein said driver possesses a hexagonal shape.

37. The drive of claim 1, wherein said handle assembly includes:
- a handle member defining a bore; and
- a sleeve positioned in said bore of said handle member, said sleeve defining said interior and having said first cam finger.

* * * * *